United States Patent
Gartner et al.

(10) Patent No.: US 8,975,441 B2
(45) Date of Patent: Mar. 10, 2015

(54) PROCESS FOR PREPARING 2.2-DIBROMOMALONAMIDE

(75) Inventors: Charles D. Gartner, Midland, MI (US); Dawn Carsten, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 133 days.

(21) Appl. No.: 12/949,325

(22) Filed: Nov. 18, 2010

(65) Prior Publication Data

US 2011/0123641 A1    May 26, 2011

Related U.S. Application Data

(60) Provisional application No. 61/263,423, filed on Nov. 23, 2009.

(51) Int. Cl.
    *C07C 231/06*    (2006.01)
    *C07C 233/05*    (2006.01)
    *A01N 37/30*    (2006.01)

(52) U.S. Cl.
    CPC .............. *C07C 231/06* (2013.01); *A01N 37/30* (2013.01)
    USPC .......................................... 564/130; 564/160

(58) Field of Classification Search
    USPC .................... 564/130, 160; 514/616; 424/616
    See application file for complete search history.

(56) References Cited

U.S. PATENT DOCUMENTS

| | | |
|---|---|---|
| 3,608,087 A | 9/1971 | Patchett et al. |
| 3,751,444 A | 8/1973 | Solem et al. |
| 4,241,080 A | 12/1980 | Burk |
| 4,518,413 A | 5/1985 | Swerdloff et al. |
| 4,800,082 A | 1/1989 | Karbowski et al. |
| 5,482,971 A | 1/1996 | Epstein et al. |
| 5,723,486 A | 3/1998 | Wu et al. |
| 6,228,633 B1 | 5/2001 | Oriel et al. |
| 2010/0314319 A1* | 12/2010 | Yin et al. .................... 210/638 |
| 2012/0177745 A1* | 7/2012 | Singleton et al. ........... 424/616 |

FOREIGN PATENT DOCUMENTS

| WO | 9801451 A1 | 1/1998 |
|---|---|---|
| WO | 2008091453 A1 | 7/2008 |

OTHER PUBLICATIONS

Katritzky et al., "Efficient Conversion of Nitriles to Amides with Basic Hydrogen Peroxide in Dimethyl Sulfoxide", Synthesis, Georg Thieme Verlag, Stuttgart, No. 12, 1989, p. 949-950.
Kim et al., "Conversion of nucleophilic halides to electrophilic halides: efficient and selective halogenation of azinones, amides, and carbonyl compounds using metal halide/lead tetraacetate", Synlett, 2006, No. 2, pp. 194-200.
International Search Report and Written Opinion for PCT/US2010/057211 dated Feb. 15, 2011.

* cited by examiner

*Primary Examiner* — Shailendra Kumar
(74) *Attorney, Agent, or Firm* — Tifani M. Edwards

(57) ABSTRACT

The present invention generally relates to a process for preparing 2,2-dibromomalonamide from 2,2-dibromo-3-cyanoacetamide.

5 Claims, No Drawings

US 8,975,441 B2

PROCESS FOR PREPARING 2.2-DIBROMOMALONAMIDE

CROSS-REFERENCE TO RELATED APPLICATIONS

This application claims benefit from U.S. Provisional Patent Application No. 61/263,423, filed Nov. 23, 2009, the entire contents of which are hereby incorporated herein by reference.

BACKGROUND OF THE INVENTION

1. Field of the Invention

The present invention generally relates to a process for preparing 2,2-dibromomalonamide.

2. Description of the Related Art

Compound 2,2-dibromomalonamide is useful as, among other things, a product, starting material, and ingredient in chemical industry and allied industries such as the microbial control industry.

U.S. Pat. No. 4,241,080 mentions, among other things, 2,2-dibromomalonic diamide (i.e., 2,2-dibromomalonamide) and preparations thereof. An example of the preparations are an acid catalyzed reaction of the corresponding non-halogenated amide, malonic diamide (i.e., malonamide), with halogen, especially bromine, in aqueous solution.

Chemical and the allied industries desire an improved process for preparing 2,2-dibromomalonamide in high yield and selectivity.

BRIEF SUMMARY OF THE INVENTION

The present invention relates to a process for preparing 2,2-dibromomalonamide from 2,2-dibromo-3-cyanoacetamide.

In a first embodiment, the present invention is a process for preparing 2,2-dibromomalonamide, the process comprising contacting together an amount of 2,2-dibromo-3-cyanoacetamide and an effective amount of a nitrile-amide-conversion composition to form a reaction mixture, the contacting being performed in such a way so as to produce 2,2-dibromomalonamide.

In a second embodiment, the present invention is a process for converting a first biocidal formulation to a second biocidal formulation, the process comprising providing a first biocidal formulation comprising a first amount of 2,2-dibromo-3-cyanoacetamide and water, contacting together the first biocidal formulation and an effective amount of a nitrile-amide-conversion composition to form a reaction mixture comprising a second biocidal formulation, the second biocidal formulation comprising water and 2,2-dibromomalonamide, the contacting being performed in such a way so as to produce (in situ) the second biocidal formulation.

The invention process is useful for preparing 2,2-dibromomalonamide and biocidal formulations comprising 2,2-dibromomalonamide, water, and, optionally at least one other biocidal formulation ingredient. The 2,2-dibromomalonamide prepared by the invention process is useful as a product (e.g., specialty chemical), starting material (e.g., in the synthesis of pharmaceutical compounds), and ingredient (e.g., as a component of antimicrobial compositions) in chemical industry and allied industries such as the microbial control industry. The biocidal formulations prepared by the invention process are useful in conventional biocidal applications such as, for example, controlling microorganisms in water systems (e.g., water cooling towers).

Additional embodiments are described in the remainder of the specification, including the claims.

DETAILED DESCRIPTION OF THE INVENTION

The present invention relates to a process for preparing 2,2-dibromomalonamide as summarized previously. The present invention also relates to the second biocidal formulation prepared by the invention process of the second embodiment. In some embodiments the second biocidal formulation further comprises at least one other biocidal formulation ingredient. In some embodiments the at least one other biocidal formulation ingredient comprises hydrogen peroxide. In some embodiments the at least one other biocidal formulation ingredient comprises an unreacted portion of the first amount of 2,2-dibromo-3-cyanoacetamide, the unreacted portion (i.e., second amount) of 2,2-dibromo-3-cyanoacetamide being less than the first amount of 2,2-dibromo-3-cyanoacetamide. In some embodiments the at least one other biocidal formulation ingredient comprises hydrogen peroxide and the unreacted portion of the amount of 2,2-dibromo-3-cyanoacetamide. In some embodiments the second biocidal formulation lacks an unreacted portion of the amount of 2,2-dibromo-3-cyanoacetamide (i.e., the first amount and an amount of 2,2-dibromo-3-cyanoacetamide that has reacted to form a product thereof are the same). In some embodiments the second biocidal formulation lacks hydrogen peroxide and the unreacted portion of the amount of 2,2-dibromo-3-cyanoacetamide.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Summary or Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

In an event where there is a conflict between a unit value that is recited without parentheses, e.g., 2 inches, and a corresponding unit value that is parenthetically recited, e.g., (5 centimeters), the unit value recited without parentheses controls.

In the event there is a discrepancy between a chemical name and structure, the structure controls.

As used herein, "a," "an," "the," "at least one," and "one or more" are used interchangeably. In any aspect or embodiment of the instant invention described herein, the term "about" in a phrase referring to a numerical value may be deleted from the phrase to give another aspect or embodiment of the instant invention. In the former aspects or embodiments employing the term "about," meaning of "about" can be construed from context of its use. Preferably "about" means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting essentially of," consists essentially of," and the like or the respective closed phrases "consisting of," "consists of," and the like to give another aspect or embodiment of the instant invention. In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "optionally" means "with or without." For example, "optionally at least one other biocidal formulation ingredient" means with or without at least one other biocidal formulation ingredient. The term "plurality" means two or more, wherein each plurality is independently selected unless indicated otherwise. The symbols "≤" and "≥" respectively mean less than or equal to and greater than or equal to. The symbols "<" and ">" respectively mean less than and greater than.

As used herein, the term "amide" means a carboxamide (i.e., a compound having a triradical functional group having a structure —C(=O)—N<) unless otherwise noted.

The term "2,2-dibromo-3-cyanoacetamide" means the compound of formula (A):

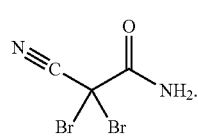

(A)

Other names for 2,2-dibromo-3-cyanoacetamide are 2,2-dibromo-3-nitrilopropionamide and DBNPA.

The term "2,2-dibromomalonamide" means a compound of formula (B):

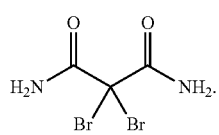

(B)

Other names for 2,2-dibromomalonamide are 2,2-dibromomalonic diamide; 2,2-dibromopropanediamide; and DBMAL.

As mentioned previously, the invention process employs the effective amount of the nitrile-amide-conversion composition. The term "effective amount" means a quantity sufficient to yield at least 50% of 2,2-dibromomalonamide from a particular reaction in question (e.g., the process of the first embodiment), the percent yield being based on the amount of 2,2-dibromomalonamide that has reacted to form a product thereof. Examples of the product are 2,2-dibromomalonamide and any reaction by-products. The amount of 2,2-dibromo-3-cyanoacetamide reacted is equal to the first amount of 2,2-dibromo-3-cyanoacetamide minus an amount of unreacted 2,2-dibromo-3-cyanoacetamide. Preferably the quantity is about just enough hydrogen peroxide to consume all of 2,2-dibromo-3-cyanoacetamide and leaving less than 5% unreacted hydrogen peroxide, more preferably less than 2% unreacted hydrogen peroxide, still more preferably less than 1% unreacted hydrogen peroxide, and even more preferably less than 0.5% unreacted hydrogen peroxide. Typically the quantity is from 2.0 moles to 2.2 moles, and more likely from 2.0 moles to 2.1 moles of hydrogen peroxide per 1.0 mole of 2,2-dibromo-3-cyanoacetamide.

Preferably, the nitrile-amide-conversion composition comprises hydrogen peroxide or a mixture comprising water and a catalytic amount of a nitrile hydratase enzyme.

In some embodiments the nitrile-amide-conversion composition comprises water and the catalytic amount of a nitrile hydratase enzyme. Nitrile hydratase enzymes comprise a family of mononuclear iron enzymes and non-corrinoid cobalt enzymes that catalyze hydration of structurally diverse nitriles to their corresponding amides (carboxamides). Nitrile hydratase enzymes are also known by other names such as NHase, nitrilase, aliphatic-amide hydro-lyase, and nitrile hydro-lyase. Preferred nitrile hydratase enzymes are those having Enzyme Commission (EC) number 4.2.1.84 and are found in mesophilic microorganisms such as, for example, *Bacillus*, *Norcardia*, *Bacteridium*, *Rhodococcus*, *Micrococcus*, *Brevibacterium*, *Alcaligenes*, *Acinetobacter*, *Corynebacterium*, *Fusarium*, and *Klebsiella*. Any nitrile hydratase enzyme is suitable for use in the invention process. One example of such nitrile hydratase enzymes is produced by a thermophilic strain of *Bacillus* sp. BR449 as described in U.S. Pat. No. 6,228,633 B1. The nitrile hydratase of U.S. Pat. No. 6,228,633 B1 is characterizable as having activity for hydrolyzing a nitrile functional group to an amide functional group at a temperature ranging from 20 degrees Celsius (° C.) to 70° C. and at a pH of from about 5 to 9.

More preferably, the nitrile-amide-conversion composition comprises hydrogen peroxide and water. Still more preferably, the nitrile-amide-conversion composition comprises hydrogen peroxide, water, and a catalytic amount of an alkali earth metal base that is an alkali earth metal hydroxide or alkali earth metal carbonate. The term "alkali earth metal" means a cationic form of lithium, sodium, potassium, cesium, magnesium, calcium, strontium, or barium; preferably of sodium, potassium, magnesium, or calcium; and more preferably sodium. In some embodiments the nitrile-amide-conversion composition comprises, or consists essentially of, water, hydrogen peroxide (i.e., $H_2O_2$), and the catalytic amount of an alkali earth metal base comprising an alkali earth metal hydroxide, alkali earth metal carbonate, alkali earth metal bicarbonate, or a mixture of any two or more thereof. In some embodiments the nitrile-amide-conversion composition further comprises, or consists essentially of, 2,2-dibromomalonamide, mother liquor from a prior run of the invention process of the first embodiment as described later, or both.

It has been discovered and is believed that, desirably, the alkali earth metal base acts catalytically in the reaction of the hydrogen peroxide with the 2,2-dibromo-3-cyanoacetamide to give 2,2-dibromomalonamide according to the invention process, thereby providing a preferred base-catalyzed invention process. While it is believed that reaction rate of the reaction of the invention process decreases as pH decreases, the reaction rate remains satisfactory for economic commercial production of 2,2-dibromomalonamide down to pH 4.0 of the nitrile-amide-conversion composition.

It has been discovered and is believed that the alkali earth metal base, which in some embodiments is part of the nitrileamide-conversion composition, acts at basic pH values (i.e., at pH values greater than pH 7.0) to undesirably promote degradation of 2,2-dibromo-3-cyanoacetamide to undesirable products. In contrast, the 2,2-dibromomalonamide is substantially more stable (i.e., 10 times or greater) at basic pH values than 2,2-dibromo-3-cyanoacetamide. As pH of the nitrile-amide-conversion composition becomes increasingly basic, the alkali earth metal base degrades increasing amounts of 2,2-dibromo-3-cyanoacetamide. This base-promoted degradation of 2,2-dibromo-3-cyanoacetamide is especially prevalent at pH 9.0 and higher. The invention process advantageously maintains pH of the reaction mixture in situ during conversion of 2,2-dibromo-3-cyanoacetamide to 2,2-dibromomalonamide in a pH range that minimizes or prevents base-promoted degradation of 2,2-dibromo-3-cyanoacetamide while at the same time facilitates the base-catalyzed conversion thereof to 2,2-dibromomalonamide.

Preferably to minimize the base-promoted degradation of 2,2-dibromo-3-cyanoacetamide during the invention process, pH of the reaction mixture is maintained in situ at pH 8.9 or lower, more preferably at pH 7.9 or lower, still more preferably at pH 7.0 or lower, and even more preferably at pH<7.0. Preferably to maximize the base-catalyzed conversion of 2,2-dibromo-3-cyanoacetamide to 2,2-dibromomalonamide during the invention process, pH of the reaction mixture is maintained in situ at pH 4.0 or higher, more preferably at pH 5.0 or higher, and still more preferably at pH 5.5 or higher. In some embodiments pH of the reaction mixture is maintained in situ from pH 5.5 to pH 7.0, and more preferably from pH 5.5 to pH<7.0.

In some embodiments the invention process further comprises maintaining pH of the reaction mixture in situ within the aforementioned pH ranges in such a manner so as to produce 2,2-dibromomalonamide in at least 75 percent (%) yield, more preferably at least 80% yield, still more preferably at least 85% yield, and even more preferably at least 90% yield (e.g., 95% yield or greater). All yields of 2,2-dibromomalonamide herein are based upon the amount of 2,2-dibromo-3-cyanoacetamide reacted unless otherwise stated.

In some embodiments the invention process further comprises maintaining pH of the reaction mixture in situ within the aforementioned pH ranges in such a manner so as to produce 2,2-dibromomalonamide where the invention process is characterized as having selectivity for conversion of 2,2-dibromo-3-cyanoacetamide to 2,2-dibromomalonamide in the presence of any other optional formulation ingredient, especially other formulation ingredients that might otherwise react with 2,2-dibromo-3-cyanoacetamide, hydrogen peroxide, or both if pH of the reaction mixture is not maintained in situ in the aforementioned pH ranges. Some examples of other formulation ingredients are polyethylene glycols, polypropylene glycols, polyethylene glycol ethers, polypropylene glycol ethers, alcohols (e.g., methanol, ethanol, and propanols), and poly(ethylene oxide)-propylene oxide copolymers, and blends thereof. Examples of still other formulation ingredients are surfactants, ionic polymers, non-ionic polymers, scale formation inhibitors, and corrosion inhibitors. Preferably, the other formulation ingredients are compatible with hydrogen peroxide, 2,2-dibromo-3-cyanoacetamide, or still more preferably both hydrogen peroxide and 2,2-dibromo-3-cyanoacetamide. As used herein, the term "compatible" means capable of forming a homogeneous mixture that neither separates nor is irreversibly altered by chemical interaction nor chemically degrades the other components. More preferably, the invention process further comprises maintaining in situ pH of the reaction mixture within the aforementioned pH ranges in such a manner so as to produce 2,2-dibromomalonamide in both of the aforementioned yields and selectivity.

The invention process provides an in situ means of maintaining pH of the reaction mixture within the aforementioned pH ranges by adding in an addition rate-controlled manner a measured amount of the hydrogen peroxide, alkali earth metal base; or more preferably independently adding in separate addition rate-controlled manners measured amounts of each of the hydrogen peroxide and alkali earth metal base. More preferably the addition rate-controlled manners comprise controlling flow rates of separate feed streams of the hydrogen peroxide (e.g., as an aqueous mixture) and alkali earth metal base (e.g., as an aqueous mixture).

In some embodiments the invention process further comprises a step comprising purifying at least some of the 2,2-dibromomalonamide to give 2,2-dibromomalonamide in substantially pure form (i.e., 90 percent or greater, more preferably 95% or greater, and still more preferably 97% or greater, all not counting water and measured using the high performance liquid chromatography method described later). For example, 100.0 grams (g) of a wet filtercake comprising 25.0 g water and 67.5 g or more of 2,2-dibromomalonamide would be substantially pure. Likewise, 100.00 g of a dry filtercake comprising 0.50 g of water and 89.55 g or more of 2,2-dibromomalonamide would be substantially pure. In some embodiments the substantially pure 2,2-dibromomalonamide can be used in a further manufacturing process step. In the further manufacturing process step, the substantially pure 2,2-dibromomalonamide can comprise, for example, a starting material in a synthesis of an organic compound (e.g., a pharmaceutical) or an ingredient in a synthesis or preparation of a biocidal composition comprising or prepared from the 2,2-dibromomalonamide. In some embodiments the invention process further comprises a step comprising drying the substantially pure 2,2-dibromomalonamide to give 2,2-dibromomalonamide in substantially pure and dry form, which preferably contains less than 2 wt %, and more preferably less than 1 wt % of water.

Reaction step(s) (e.g., as opposed to purification or drying steps) of the invention process produces the reaction mixture that ultimately comprises 2,2-dibromomalonamide, and, possibly, one or more other components. Examples of the possible other components are unreacted starting materials (e.g., unreacted 2,2-dibromo-3-cyanoacetamide, $H_2O_2$, or alkali earth metal base), solvent(s) (e.g., water), reaction by-products, base-promoted degradation product(s) of 2,2-dibromo-3-cyanoacetamide, or a combination thereof. Solubility of the 2,2-dibromomalonamide in the reaction mixture can depend upon particular conditions employed (e.g., temperature, pH, formulation composition, or a combination thereof). The 2,2-dibromomalonamide can be in a form of a solute dissolved in the reaction mixture, a solid disposed (e.g., dispersed or suspended) in a reaction liquid, or both. Preferably at least 90% of the 2,2-dibromomalonamide produced by the invention process is in the form of the solid disposed in the reaction liquid. The solid 2,2-dibromomalonamide can be readily removed or separated from its reaction liquid, and thus from any reaction liquid-soluble materials. In some embodiments the solid 2,2-dibromomalonamide is removed by filtering to separately give an aqueous mother liquor filtrate and a wet solid filtercake comprising 2,2-dibromomalonamide and residual water, the 2,2-dibromomalonamide of the wet solid filtercake being in substantially pure form as described previously. In some embodiments the wet solid filtercake containing 2,2-dibromomalonamide is used without further purification or drying to prepare a biocidal formulation. In other embodiments the wet solid filtercake containing 2,2-dibromomalonamide is dried by conventional means (e.g., vacuum drying or drying by contacting a gas stream to the solid (e.g., flowing the gas stream over or through the solid)) to give a dry solid filtercake comprising 2,2-dibromomalonamide in substantially pure and dry form as described previously.

Preferably, the invention process further comprises a step of employing a portion or all the mother liquor in another run of the invention process of the first embodiment. Each such subsequent run of the invention process of the first embodiment preferably uses a mother liquor of a previous run, thereby establishing a means for recycling a mother liquor from an initial run of the invention process two or more, more preferably 3 or more, and still more preferably 5 or more times.

Reaction temperature, pressure, and time are not critical for performing any of the reactions, purifications, or dryings of the invention process. Any reaction temperature, pressure, and time is suitable provided the starting materials (e.g., compound of formula (A)) do not substantially decompose or otherwise undesirably react thereat. For example, suitable temperatures and pressures for preparing 2,2-dibromomalonamide are from 0° C. to 100° C., preferably from 20° C. to 50° C., and about ambient pressure (e.g., about 101 kilopascals (kPa)). Examples of a suitable temperature and pressure for drying wet solid 2,2-dibromomalonamide are from 20° C. to 100° C., preferably from 20° C. to 60° C. (e.g., 50° C.), and about ambient pressure or lower (e.g., down to about 1 kPa).

The 2,2-dibromo-3-cyanoacetamide can be prepared by any known synthetic method (e.g., dibromination of 3-cyanoacetamide) or preferably obtained from a commercial supplier. There are several commercial suppliers of 2,2-dibromo-3-cyanoacetamide and all of the commercially supplied versions of 2,2-dibromo-3-cyanoacetamide are acceptable for use in the invention. Further, commercially formulated forms of 2,2-dibromo-3-cyanoacetamide such as, for example, a formulation of 2,2-dibromo-3-cyanoacetamide and polyethylene glycol blends in water can be used in the invention.

Materials and General Methods

Reactants:
2,2-dibromo-3-cyanoacetamide, The Dow Chemical Company, batch #W126xxxxC2; molecular weight 241.87 grams per mole (g/mol).
50 wt % aqueous hydrogen peroxide—Sigma-Aldrich—material #516813-4L, batch #55798PJ.
6 wt % aqueous sodium hydroxide
Deionized water.

Equipment:
Vacuum filter flask.
A 22-liter baffled glass stirred reactor (i.e., stirable reactor) having a flush mount bottom drain valve. The stirred reactor has multiple top ports for additions, sensor entry. Six ports of the stirred reactor are equipped as follows:
1) pH probe—portable pH meter (Accumet AP62 pH/mv meter with Orion pH probe)
2) 1000 mL addition funnel for adding the 50 wt % aqueous hydrogen peroxide
3) Stirrer—electric stir shaft and Teflon paddle with 4 blades
4) Two temperature thermocouples, each wired to a different digital temperature display
5) 250 mL addition funnel for adding the 6 wt % aqueous sodium hydroxide
6) A vent to atmosphere or, if desired, a scrubbing device Use a 22-liter, glass storage tank to store mother liquor between runs. Use a Masterflex® peristaltic pump (Cole-Parmer Instrument Company, Vernon Hills, Ill., USA) both to pump the mother liquor from a 4-liter vacuum filter flask to the storage tank and pump a recycle charge back from the storage tank into the stirred reactor for a subsequent run. Use a porcelain Buchner funnel outfitted with a medium porosity filter paper (18.5 centimeter diameter) disposed on the 4-liter vacuum flask. Supply vacuum from a water aspirator.

EXAMPLE(S) OF THE PRESENT INVENTION

Non-limiting examples of the present invention are described below. In some embodiments the present invention is as described in any one of the examples.

Example 1

Preparation of 2,2-dibromomalonamide Using Deionized Water

Performing reaction: Fill stirred reactor with about 16 liters of deionized water. Add 2,2-dibromo-3-cyanoacetamide (1997.4 g, 8.258 mol) with stirrer agitation at an agitation rate. When all the 2,2-dibromo-3-cyanoacetamide is in the reactor, increase the agitation rate (i.e., speed of the stirrer) to ensure solid suspension of the 2,2-dibromo-3-cyanoacetamide. Starting pH of this starting suspension is pH 6.3. Start slow addition of the 50 wt % aqueous hydrogen peroxide (a total of 1180.8 g of 50 wt % aqueous hydrogen peroxide, containing 17 mol $H_2O_2$ (molecular weight 34.015 g/mol), are ultimately added). Once pH of resulting mixture decreases to pH 3.9, start adding 6 wt % aqueous sodium hydroxide (a total of 251.8 g of 6 wt % aqueous sodium hydroxide, containing 0.38 mol NaOH (molecular weight 40.00 g/mol), are ultimately added). A thick layer of foam may develop and possibly push out of the vent of the stirred reactor. Ensure rate of addition of the 50 wt % aqueous hydrogen peroxide is slow enough to allow the foam layer to dissipate or further increase the agitation rate to aid dispersion and breaking of the foam. After about half of the 50 wt % aqueous hydrogen peroxide is added, the resulting reaction mixture (a slurry) is noticeably thinner than the starting suspension and temperature of the reaction slurry peaks at 51° C. The pH stays around pH 5.5 to pH 5.7 during addition of the 50 wt % aqueous hydrogen peroxide. The time for adding the 50 wt % aqueous hydrogen peroxide is 4.13 hours. Stir the slurry for about 1 hour, and then allow the slurry to settle overnight while slowly cooling to room temperature (about 25° C.).

Filtering of the reaction mixture to isolate solids comprising 2,2-dibromomalonamide as a filtercake and collection and storage of mother liquor for use in next run: Next morning the resulting reaction mixture comprises solids, different portions of which are floating on, settled at bottom of, or suspended in the reaction mixture. Turn on stirrer to disperse the solids in the liquid, and then filter the reaction mixture using the Buchner funnel to collect the wet solids comprising 2,2-dibromomalonamide and the filter flask to collect mother liquor as a filtrate. The wet solid 2,2-dibromomalonamide contains 19.6 wt % of volatile material (e.g., water) that can be removed by drying. Pump mother liquor out of the filter flask and into the storage tank for recycling thereof into a subsequent reaction in place of deionized water in Example 2 (described later).

Drying filtercake solids comprising 2,2-dibromomalonamide: transfer filtercake solids to a metal or a plastic tray.

Place trays into a makeshift "drying chamber" that is constructed such that dry nitrogen gas or a dry air stream can be passed over the solids. Turn gas on and allow it to flow over the solids in the trays until a constant weight is achieved to yield 1752 grams (g) of gas-dried 2,2-dibromomalonamide (yield of 81.6% based on the 2,2-dibromo-3-cyanoacetamide that is added; 2,2-dibromomalonamide molecular weight 259.88 g/mol). Results are shown later in Table 1.

Examples 2 to 7

Preparations of 2,2-dibromomalonamide Using a Recycled Mother Liquor Instead of Deionized Water In each of Examples 1 to 7, the molar ratio of $H_2O_2$ to 2,2-dibromo-3-cyanoacetamide is about 2.06. Repeat the procedure of Example 1 except use none or trivial amount of deionized water and instead use mother liquor from a previous reaction mixture in place of the deionized water of Example 1. Example 2 uses 15 L of mother liquor from Example 1. Examples 3 to 7 each use 13 L of mother liquor from Examples 2 to 6, respectively. A reduction in recycled mother liquor is used to lessen the potential of foam pushing out the stirred reactor vent. No segregation of the mother liquors from different batches is needed; a mixture of mother liquors from several reactions are suitable for being recycled. The wet solid 2,2-dibromomalonamide batches of Examples 2 to 7 respectively contain 32.8 wt %, 26.9 wt %, 24.7 wt %, 17.9 wt %, 28.6 wt %, and 26.0 wt % of volatile material (e.g., water). Dry the wet solid 2,2-dibromomalonamide as described previously in Example 1 to respectively give gas-dried solid 2,2-dibromomalonamide of Examples 2 to 7.

Results are shown below in Table 1. In Table 1, Ex. No. means Example Number, g means grams, DBNPA means 2,2-dibromo-3-cyanoacetamide, wt % means weight percent, h means hours, DBMAL means 2,2-dibromomalonamide, and % means percent.

TABLE 1 results of Examples 1 to 7

| Ex. No. | Total Weight of deionized water (g) | Weight of DBNPA (g) | Weight of 50 wt % aq. $H_2O_2$ (g) | Weight of 6 wt % aq. NaOH (g) | Time for 50 wt % aq. $H_2O_2$ addition (h) | Yield of dried DBMAL (g) | Yield of dried DBMAL (%) |
|---|---|---|---|---|---|---|---|
| 1 | 16052 | 1997.4 | 1180.8 | 251.8 | 4.13 | 1752.4 | 81.6 |
| 2 | 103 | 1999.8 | 1178.7 | 95.7 | 4.98 | 1921.7 | 89.4 |
| 3 | 137 | 2000.9 | 1180.6 | 104.6 | 3.77 | 2001.1 | 93.1 |
| 4 | 0 | 1998.2 | 1184.5 | 71.2 | 3.1 | 1992.8 | 92.8 |
| 5 | 115 | 2001.7 | 1181.9 | 28.7 | 3.18 | 2055 | 95.6 |
| 6 | 141 | 1999.7 | 1188.6 | 0 | 2.85 | 1933.2 | 90.0 |
| 7 | 23 | 2001.5 | 1180.9 | 77.6 | 2.55 | 1972.4 | 91.7 |

Blend the gas-dried 2,2-dibromomalonamide of Examples 1 to 7 together. Dry a 502.46 g portion of the combined gas-dried 2,2-dibromomalonamide in a vacuum oven for 5 hours at 50° C. to yield 502.03 g of vacuum-dried 2,2-dibromomalonamide. The result indicates that the combined gas-dried 2,2-dibromomalonamide of Examples 1 to 7 contain about 0.5 wt % water.

Analyze purity of the combined gas-dried 2,2-dibromomalonamide by high performance liquid chromatography (HPLC) using an Agilent Zorbax CN column (4.6 millimeter (mm) by 250 mm, 5 micron particle) and eluent comprising 80 volume percent (vol %) high purity water/20 vol % high purity acetonitrile with 0.05 molar sodium phosphate monobasic buffer, pH adjusted to pH 3 with 85 wt % phosphoric acid. Flow rate is 1.0 mL eluent per minute, injection volume 2.0 microliters, ultraviolet detection at 205 nanometers, and a run time of 15 minutes. The 2,2-dibromomalonamide component elutes at 3.62 minutes and indicates that the gas-dried 2,2-dibromomalonamide is 97.75% pure based on peak area.

As shown by the above Examples, the invention process produces 2,2-dibromomalonamide in high yields from 2,2-dibromo-3-cyanoacetamide and provides a means for recycling reaction mother liquors while minimizing amount of alkali earth metal base so as to minimize or prevent base-promoted degradation of the 2,2-dibromo-3-cyanoacetamide while at the same time providing sufficient amounts of the alkali earth metal base to catalyze the desired conversion of 2,2-dibromo-3-cyanoacetamide to 2,2-dibromomalonamide.

While the invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A process for preparing 2,2-dihromomalonamide, the process comprising contacting together an amount of 2,2-dibromo-3-cyanoacetamide and an effective amount of a nitrile-arnide-conversion composition to form a reaction mixture, the contacting being performed in such a way so as to produce 2,2-dibromomalonamide and wherein the process further comprises
   a. obtaining a mother liquor from the reaction mixture:
   b. preparing another nitrile-amide-conversion composition comprising most of the mother liquor;
   c. contacting the other nitTile-amide-conversion comprising the mother liquor to another amount of 2,2-dibrotno-3-cvanoacetamide to form another reaction mixture, the contacting the other nitrile-amide-conversion comprising the mother liquor to another amount of 2,2-dibromo-3-cvanoacetamide being performed in such a way no as to produce additional 2,2-dibromomalonamide.

2. The process as in claim 1, the process further comprising maintaining pH of the reaction mixture during the contacting step at less than pH 9.0.

3. The process as in claim 2, the process further comprising maintaining pH of the reaction mixture during the contacting step at a pH from pH 4.0 to less than pH 9.0.

4. The process as in claim 3, the process further comprising maintaining pH of the reaction mixture during the contacting step at a pH from pH 5.5 to pH 7.0.

5. The process as in claim 1, each contacting step independently producing the 2,2-dibromomalonamide in 75 percent yield or higher based on an amount of 2,2-dibromo-3-cyanoacetamide that has reacted.

* * * * *